United States Patent
Ruggero et al.

(10) Patent No.: US 11,253,522 B2
(45) Date of Patent: Feb. 22, 2022

(54) CANCER TREATMENT TARGETED TO TUMOR ADAPTIVE RESPONSES TO PROTEIN SYNTHESIS STRESS

(71) Applicant: The Regents of the University of California, Oakland, CA (US)

(72) Inventors: Davide Ruggero, Emerald Hill, CA (US); Hao Nguyen, San Francisco, CA (US); Peter Carroll, San Francisco, CA (US); Crystal Conn, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/396,723

(22) Filed: Apr. 28, 2019

(65) Prior Publication Data

US 2019/0328740 A1    Oct. 31, 2019

Related U.S. Application Data

(60) Provisional application No. 62/664,144, filed on Apr. 28, 2018.

(51) Int. Cl.

| | |
|---|---|
| *A61K 31/519* | (2006.01) |
| *A61P 35/02* | (2006.01) |
| *G01N 33/574* | (2006.01) |
| *G01N 33/573* | (2006.01) |
| *A61K 45/06* | (2006.01) |

(52) U.S. Cl.
CPC ............ *A61K 31/519* (2013.01); *A61P 35/02* (2018.01); *G01N 33/573* (2013.01); *G01N 33/57434* (2013.01); *A61K 45/06* (2013.01); *G01N 2440/14* (2013.01)

(58) Field of Classification Search
CPC ........ A61K 31/519; A61K 45/06; A61P 35/02
See application file for complete search history.

(56) References Cited

U.S. PATENT DOCUMENTS

| | | | |
|---|---|---|---|
| 9,617,601 B2* | 4/2017 | Zhang | G01N 33/48721 |
| 9,708,247 B2 | 7/2017 | Walter et al. | |
| 2006/0234259 A1* | 10/2006 | Rubin | C12Q 1/6886 |
| | | | 435/6.14 |

(Continued)

OTHER PUBLICATIONS

Wang M, Kaufman RJ. "The impact of the endoplasmic reticulum protein-folding environment on cancer development." Nat Rev Cancer. 2014; 14:581-597. [PubMed: 25145482].

(Continued)

*Primary Examiner* — Savitha M Rao

(57) ABSTRACT

In cancers such as prostate cancer, the combination of PTEN loss and activation of Myc activates an adaptive stress response that enables tumor cells to escape the stress of massively upregulated protein synthesis. This pro-survival response is mediated by the PERK-phosphorylated eIF2α axis of the UPR adaptive response. Agents that disrupt PERK-eIF2α pathways disrupt the adaptive response and lead to cancer cell death from uncontrolled growth. For example, ISRIB and derivatives may be employed as therapeutic agents to disrupt PERK-mediated adaptive mechanisms. Additionally PTEN loss and activation of Myc provides a diagnostic marker that enables better prognosis and the selection of amenable treatments.

6 Claims, 9 Drawing Sheets

(56) References Cited

U.S. PATENT DOCUMENTS

2017/0342020 A1* 11/2017 Walter ................ C07C 257/14

OTHER PUBLICATIONS

Fels DR, Koumenis C. "The PERK/eIF2α/ATF4 module of the UPR in hypoxia resistance and tumor growth." Cancer Biol Ther. 2006; 5:723-728. [PubMed: 16861899].
Robichaud N, Sonenberg N. "Translational control and the cancer cell response to stress." Curr Opin Cell Biol. 2017; 45:102-109. [PubMed: 28582681].
Liu et al., 2013. Genetic markers associated with early cancer-specific mortality following prostatectomy Cancer 119: . doi:10.1002/cncr.27954, p. 14, Table 4.

* cited by examiner

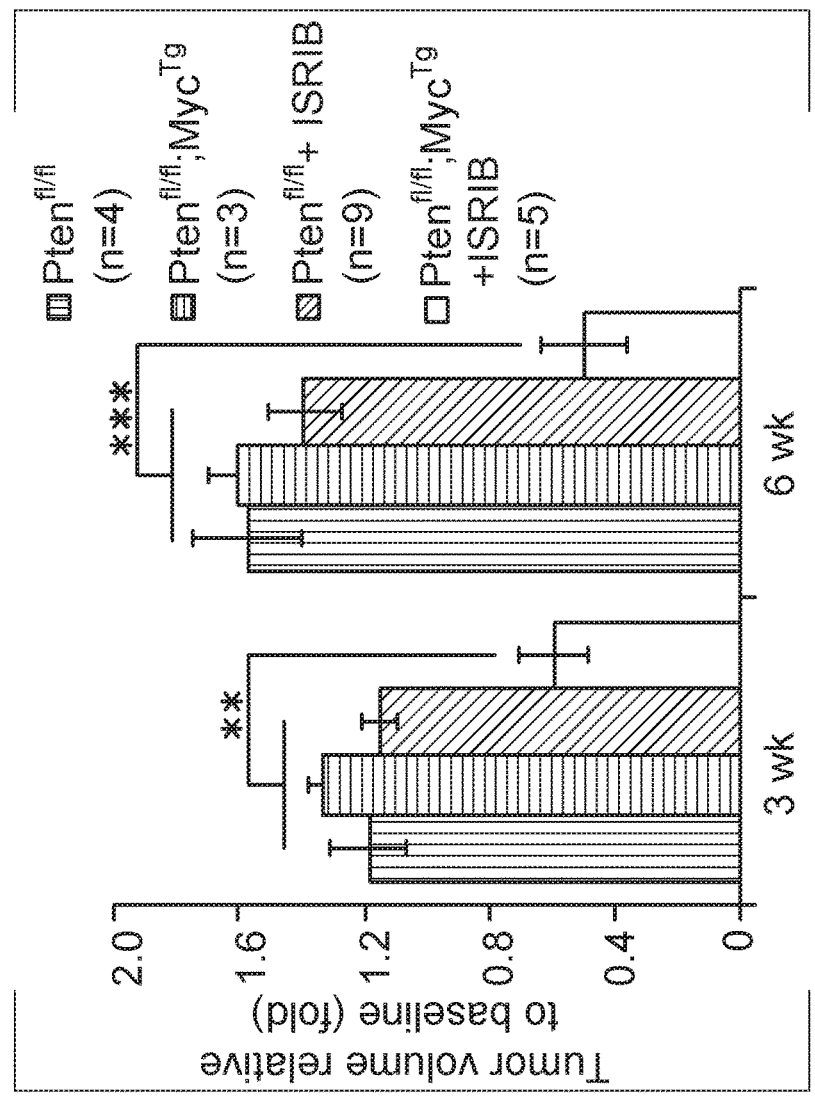
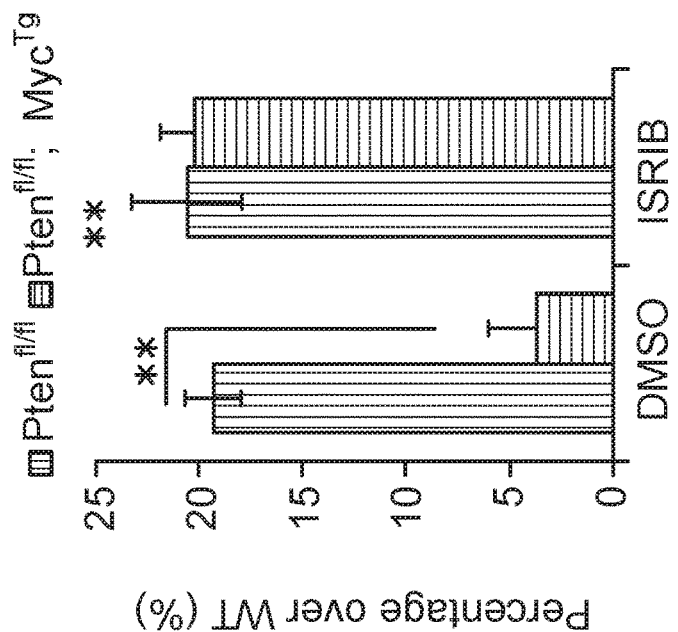
FIG. 3A
FIG. 3B

CANCER TREATMENT TARGETED TO TUMOR ADAPTIVE RESPONSES TO PROTEIN SYNTHESIS STRESS

CROSS-REFERENCE TO RELATED APPLICATIONS

This application claims the benefit of priority to U.S. Provisional Application Ser. No. 62/664,144 entitled "Cancer Treatment Targeted to Tumor Adaptive Responses to Protein Synthesis Stress," filed Apr. 28, 2018, the contents which are hereby incorporated by reference.

STATEMENT REGARDING FEDERALLY SPONSORED RESEARCH OR DEVELOPMENT

This invention was made with government support under grant number R01 CA154916 awarded by the National Institutes of Health. The government has certain rights in the invention.

BACKGROUND OF THE INVENTION

Multiple oncogenes are known to be drivers of cancer. For example, phosphatase and tensin homolog, "PTEN," as known in the art, is a tumor suppressor gene which is commonly lost by mutation in tumor cells. For example, over 70% of prostate cancer patients have mutations in PTEN. PTEN loss is generally associated with dysregulation and upregulation of protein synthesis and other processes central to cancer.

Similarly, the Myc oncogenic transcription factor is a key regulator of cell growth and proliferation. Activation of Myc, by mutations which cause its constitutive expression, are known to cause the dysregulation of numerous downstream genes and is thought to play a role in many cancers. Myc activation has also been associated with upregulation of protein synthesis rates. Various Myc mutations which cause activation are known.

The combination of Myc activation and loss of PTEN is known in the art to exert a substantial impact on the progression of certain cancers. For example, in prostate cancer, this combination has been shown to result in genetic instability and may lead to lethal metastatic prostate cancer. The combined loss of PTEN and Myc activation is also implicated in other cancers, such as T-cell acute lymphoblastic leukemia.

In prostate and other cancers, uncontrolled cell growth and division is sustained by stimulating the production of molecular building blocks, such as proteins and outputs of anabolic metabolism. One of the early consequences of many cancers is a major remodeling of the cancer cell proteome associated with increases in protein biosynthesis.

Massive upregulation of protein synthesis is an onerous expenditure of cellular resources, and it remains poorly understood how cancer cells adapt to this increased metabolic load. One example is an increase in total proteins being synthesized, because cancer cells need to sustain augmented growth and division. For instance, more than 65% of the energy in the cell is devoted to the bioenergetically expensive process of protein synthesis that is greatly increased in most cancers.

Left unchecked, infinite increases in the cancer cell's biosynthetic demand would tilt the balance from continuous growth and division to cell death. Therefore, increased rates of biosynthetic processes place a high demand on cancer cells and are a source of constant stress that must be carefully regulated by the activation of appropriate checkpoints, which remain poorly understood. Increased protein synthesis and the flux in the endoplasmic reticulum (ER) create a state of proteotoxic stress associated with the accumulation of misfolded proteins. This ER stress activates the unfolded protein response (UPR). The UPR is composed of three signaling arms: ATF6 (activating transcription factor 6) with transcriptional activity to promote ER homeostasis, IRE1 (inositol-requiring enzyme 1) to control splicing of the transcription factor XBP1 enhancing ER gene expression, and PERK [PKR (RNA-activated protein kinase)-like ER-associated protein kinase], which promotes downstream phosphorylation of eIF2α (eukaryotic initiation factor 2-α) (P-eIF2α) on serine 51. Unlike the other arms of the UPR, PERK P-eIF2α creates a direct "brake" for general protein synthesis because of the conversion of eIF2α from a substrate of the ternary complex, which is necessary to promote the initiation step of mRNA translation, to an inhibitor of this complex.

Although UPR activation has previously been associated with cancer, it remains poorly understood which oncogenes and/or combinations of oncogenes control distinct arms of this pathway in vivo during the initiation or progression of tumor development. It is also unclear whether and when the UPR is activated during the course of cancer evolution, or its specific requirements in distinct phases of tumorigenesis. Accordingly, there is a need in the art for an understanding of how cancer cells accommodate the overwhelming stress associated with a very high protein synthesis burden. There is a need in the art for an understanding of the cytoprotective responses activated in aggressive neoplasms. There is a need in the art for identifying points of vulnerability in cancer's adaptations to massive growth rates that can be exploited for therapeutic interventions. Additionally, there remains a need in the art for elucidation of the pathways by which the combination of PTEN loss and Myc activation work in concert to drive cancer.

SUMMARY OF THE INVENTION

The inventions disclosed herein are based on the unexpected discovery that combined PTEN loss and Myc activation results in attenuated protein synthesis rates. This observation reveals an interesting paradox, wherein, despite the presence of two oncogenic lesions that individually up-regulate protein synthesis, a previously unknown adaptive response is activated by the combined mutations, and this adaptive brake on protein synthesis provides a pro-survival means for aggressive tumors to endure the deleterious effects of high growth rates.

The inventors of the present disclosure have further discovered that the adaptive response is based upon the selective upregulation of the PERK-mediated integrated stress response (ISR) branch of the unfolded protein response (UPR). Thus, PERK activation is a distinct adaptive response that promotes tumorigenesis in aggressive cancer, driven by the unexpected cooperation of two oncogenic lesions.

Furthermore, as demonstrated in the disclosures of the present application, interventions that inhibit the adaptive response will promote the death of aggressively growing tumor cells and provide a novel target for the treatment of cancer.

Accordingly, in a first aspect, the scope of the invention encompasses novel methods of treating cancer by inhibiting adaptive responses that enable aggressive tumors to survive the stress of highly accelerated growth. The scope of the invention encompasses interventions that inhibit the PERK-eIF2α pathway, which, as shown herein, is specifically and selectively activated in cells having PTEN loss and activated Myc.

In another aspect, the scope of the invention encompasses novel methods of prognosing cancer by assessing PTEN loss and Myc activation status. As shown herein, the combination of these factors results in the promotion of tumor growth by attenuating apoptotic and other stresses that arise from enhanced protein synthesis. Cancerous cells having this phenotype are better adapted for aggressive growth and thus the phenotype provides a prognostic measure.

In yet another aspect, the scope of the invention encompasses novel methods of treating cancer, comprising an assessment of PTEN loss and Myc activation status in the cancerous cells of a subject, and the selection and administration of an appropriate treatment based thereon.

BRIEF DESCRIPTION OF THE DRAWINGS

FIG. 1A depicts total dehydrated prostate weights from 6-week-old mice and FIG. 1B depicts total dehydrated prostate weights from 10-week-old mice, averaged for each genotype (n=3 to 6 mice per arm, mean±SEM). wild-type, WT. FIG. 1C depicts phenotypical penetrance percentages for low-grade prostatic intra-epithelial neoplasia (LgPIN), HgPIN, and cancer in anterior prostate tissues from 6- and 10-week-old mice evaluated by hematoxylin and eosin (H&E) staining. FIG. 1D depicts quantification of prostate tumor size in mice with an average age of 8 months (n=5 mice per arm, mean±SEM). FIG. 1F depicts newly synthesized proteins measured by $^{35}$S methionine/cysteine incorporation in organoids relative to WT littermates (n=5, mean±SEM). *P<0.05, P<0.01, *P<0.001, t test.

FIG. 2 depicts P-PERK expression and P-eIF2α expression, quantified relative to DAPI (n=3 mice per arm, with four images averaged per mouse, mean±SEM).

FIGS. 3A and 3B. FIG. 3A depicts quantification of radioactive pulse relative to loading, depicted as percent over WT (n=3, mean±SEM). FIG. 3A depicts quantification of tumor size as fold change relative to baseline volume at 3- and 6-week time points (mean±SEM). P<0.01, *P<0.001, t test.

FIG. 4A depicts quantification of annexin V-positive cells analyzed by flow cytometry relative to control cells after treatment with DMSO or 500 nM ISRIB for 9 hours (n=3, mean±SEM) *P<0.05, t test. FIG. 4B depicts Cox proportional hazards regression results in a Forest plot of hazard ratios and 95% CI for factors associated with risk of clinical progression after surgery. Independent factors are tumor with PTEN loss/low P-eIF2α or PTEN loss/high P-eIF2α versus a reference group with normal PTEN expression; age in years; PSA in nanograms per milliliter; Gleason score >7 versus 6; and pathological stage T3-T4 versus T2 at the time of prostatectomy.

FIGS. 5A, 5B, and 5C depict quantification of protein expression as relative mean IF intensity normalized to adjacent stromal tissue for: FIG. 5A: benign, FIG. 5B PCa, and mPCa cell types. FIG. 5D and FIG. 5E depict Kaplan-Meier tumor survival curves for mice bearing pPCa (5D) or mPCa (5E) tumors treated with ISRIB (10 mg/kg) or vehicle (n=8, per cohort; P=0.01, log-rank test). The survival curves represent mice euthanized when tumors reached an end point of 2 cm or when the mice showed clear signs of morbidity. FIG. 5F depicts quantification of PDX tumors treated with vehicle or ISRIB (10 mg/kg); (n=3, *P<0.001, t test). FIG. 5G depicts quantification of newly synthesized proteins in vivo, assessed by incorporation of OP-Puro within PDX treated with ISRIB (10 mg/kg) or vehicle (n=3 to 4 per arm, mean±SEM; *P<0.05, t test). n.s., not significant. MFI, mean fluorescence intensity.

DETAILED DESCRIPTION OF THE INVENTION

Figure 1B:
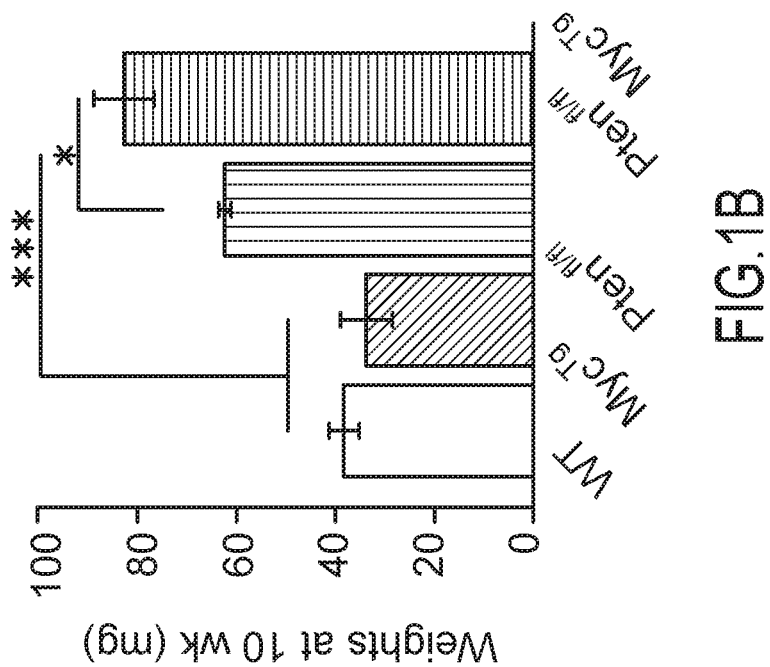
FIGS. 1A, 1B, 1C, 1D, 1E, and 1F.
Figure 1A:
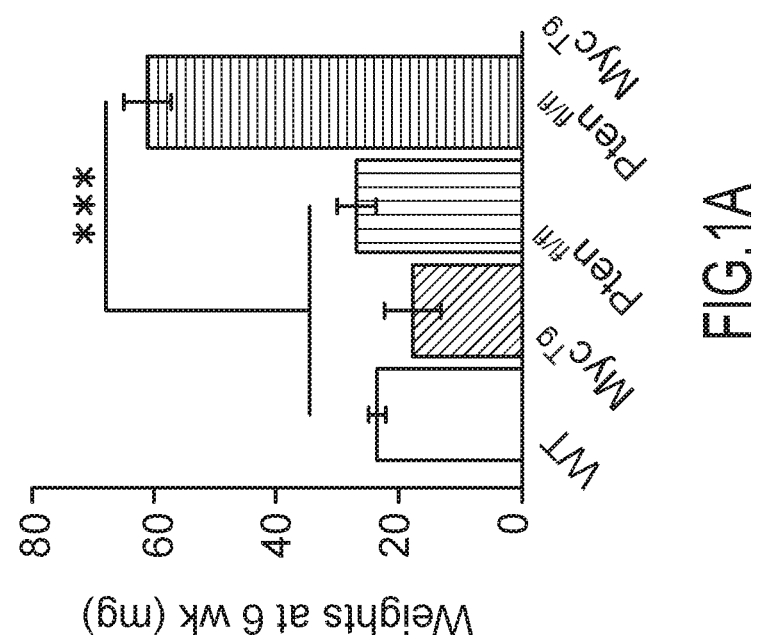

The invention is directed to various aspects of cancer prognosis and treatment in a subject. The subject may comprise a human patient, or may comprise a non-human animal, for example a test animal or veterinary subject. The scope of the invention also extends to the treatment of cultured cancer cells, cancer explants, or other in vitro uses. The subject may comprise a subject at risk of cancer, a subject at risk of cancer recurrence, a subject having one or more tumors, or a subject that has previously had tumors or other cancerous cells removed from the body, for example, by surgical resection, or has had cancerous cells ablated by a treatment such as radiation therapy, chemotherapy, or immunotherapy.

In various implementations, the subject has or has had cancer, i.e. has or has had cancerous cells in the body, for example, one or more tumors. Cancerous cells, as used herein, may be precancerous cells, tumor cells, metastasizing cells, or other cells indicative of cancer risk or cancer. The cancerous cells may be those of any neoplastic condition known in the art, for example, a cancer selected from the group consisting of bladder cancer, brain cancer, breast cancer, cervical cancer, colorectal cancer, esophageal cancer, head and neck cancer, kidney cancer, lung cancer, leukemia, lymphoma, myeloma, ovarian cancer, pancreatic cancer, sarcoma, and skin cancer. In one embodiment, the cancer is prostate cancer. For example, the subject may comprise a subject having prostate cancer, at risk of prostate cancer, or a post-surgical subject at risk of prostate cancer recurrence. In some embodiments, the cancerous cells are leukemia cells, for example, T-cell acute lymphoblastic leukemia cells. In some implementations, the cancer comprises a primary tumor. In some implementations, the cancer comprises a metastasis.

In some implementations, the methods of the invention may be applied for the treatment of cancer. "Treatment," as used herein, comprises any preventative or therapeutic treatment of cancer, including, for example: prevention of cancer; slowing the progression of cancer; preventing the recurrence of cancer; preventing metastasis; reducing tumor size; slowing tumor growth, and increasing survival time.

Certain methods described herein are accomplished by the administration of a pharmaceutically effective amount of an agent. A pharmaceutically effective amount, as used herein, means for example, an amount sufficient to cause a measurable biological response, an amount sufficient to cause measurable disruption of adaptive ISR responses, or an amount sufficient to cause any measurable therapeutic effect.

The agents of the invention may be administered at any safe and efficacious dosage, determined as known in the art for the selected agent. Exemplary dosages may be, for example, in the range of 1 ng agent to 1,000 milligram of agent, depending on the potency, ADMET, and side effects of the selected agent. Exemplary dosages are in the range of 1-100 ng, 100-1,0000 ng, 1 to 100 micrograms, 100-500 micrograms, 500-1,000 micrograms, 1 to 100 mg, 100-500 mg, or 100-1,000 mg. Dosages may be administered, for example, daily, multiple times per week, weekly, monthly, or as otherwise effective for the selected agent.

The agents of the invention may be administered in any manner compatible with their physical and pharmacological properties. Administration may be systemic or localized. For example, administration may be orally, intravenously, topically, by intraperitoneal injection, or by intratumoral injection.

The agents of the invention may be administered in combination with any pharmaceutically acceptable carrier, excipient, or delivery vehicle. The agent may be co-administered in combination with any other therapeutic composition, for example an immunotherapy or chemotherapeutic agent.

PTEN Loss and Myc Activation.

In a primary implementation of the invention, the methods of the invention are applied to a subject wherein cancerous cells of the subject have a combination of both: (1) PTEN loss and (2) Myc activation. Accordingly, certain aspects of the invention encompass an assessment of PTEN loss in cancerous cells. PTEN means the phosphatase and tensin homolog, as known in the art. PTEN loss, as used herein, means any reduction or absence of PTEN expression in a cancerous cell. PTEN loss, may include, for example, any reduction in PTEN expression, any reduction in PTEN protein abundance or activity, or any loss (e.g. deletion) of the PTEN gene or the downregulation of the PTEN gene. "Reduction," in the context of PTEN loss means an observed reduction compared to a selected baseline tissue. For example, in one embodiment, the assessment of PTEN loss in cancerous cells is made by comparing a measure of PTEN expression in the cancerous cells against the selected measure of PTEN expression in non-cancerous tissue, for example, from the vicinity of the cancerous cells. Any relevant benign stromal cell can be utilized to establish the baseline. For example, the comparison of PTEN expression may be made by use of cancerous cells and adjacent or intermixed non-cancerous cells in a sample, for example, a sample comprising a biopsy or resected tumor. For example, in the case of a resected tumor, non-cancerous cells in the surgically removed margin may be used as the source of non-cancerous cells for comparison of PTEN expression. In one embodiment, the comparison is made against average PTEN expression levels in benign cells of like subjects (for example from matched patient pools, e.g., matched by age, demographic factors, disease factors, or other relevant matching factors). For example, PTEN expression of cancerous cells from a prostate tumor may be compared against average PTEN expression in benign prostate tissue observed in a population of like subjects.

PTEN loss may be any loss or reduction compared to the selected baseline, for example, a reduction in PTEN expression of at least 5%, at least 10%, at least 20%, at least 30%, at least 40%, at least 50%, at least 60%, at least 70%, at least 80%, at least 90%, or at least 95% reduced, compared PTEN expression or abundance of the selected baseline. Statistically significant cutoff or threshold values for determination of PTEN loss may be established, by methods known in the art.

Certain aspects of the invention encompass an assessment of Myc activation. Myc activation, as used herein, may encompass any substantial or elevated expression of the c-myc gene and the presence or activity of its expression protein, the c-myc transcription factor. Activated Myc may encompass upregulated c-Myc expression, or constitutive c-Myc expression, for example, by the action of mutations in the Myc promotor or by the action of upstream species which regulate Myc expression, for example, by the action of upstream species which regulate the translation of MYC mRNA, MYC degradation or MYC mRNA stability. As with PTEN loss, Myc activation in cancerous cells may be established by comparison to a selected baseline. In one embodiment, the baseline is Myc expression in adjacent, benign non-cancerous cells. In one embodiment, the baseline is population average Myc expression in benign tissues of the same type as the cancerous cells (e.g. comparing Myc expression in cells of a prostate tumor to population average Myc expression in benign prostate tissues).

Designation of Myc activation may be defined by exceeding a selected threshold for a selected measure of Myc activation compared to the selected baseline, for example, an increase in Myc activation of at least 5%, at least 10%, at least 20%, at least 30%, at least 40%, at least 50%, at least 60%, at least 70%, at least 80%, at least 90%, or at least 95% greater than the selected baseline value.

As described below, elevated phosphorylated eIF2α levels may serve as a predictive factor equivalent to the Myc oncogene for prognosing cancer when used in combination with PTEN loss. Accordingly, certain aspects of the invention are directed to assessment of elevated phosphorylated eIF2α. Elevated phosphorylated eIF2α activation means any increase in a selected measure of phosphorylated eIF2α abundance, for example, absolute abundance or the ratio of phosphorylated eIF2α to non-phosphorylated eIF2α. "Elevated" may be any increase, for example, an increase of at least 5%, at least 10%, at least 20%, at least 30%, at least 40%, at least 50%, at least 60%, at least 70%, at least 80%, at least 90%, or at least 95% greater than the selected baseline value.

Treatment by Inhibition of Adaptive ISR.

As disclosed herein, the combination of PTEN loss and Myc activation imparts a survival advantage to cancerous cells. Specifically, the inventors of the present disclosure have determined that PTEN loss and Myc activation, in combination, promote an adaptive response to the onerous stress of highly upregulated protein synthesis by the upregulation of the adaptive mechanisms.

In the broadest implementation, the scope of the invention encompasses a method of treating cancer by inhibiting ISR processes in cancerous cells that enable the cell to escape growth stress. The scope of the invention thus extends to any intervention which disrupts a prosurvival ISR response. The ISR response inhibited in the methods of the invention may be, for example, an IRE1-mediated response, a heme-regulated eIF2α (HRI), general control non-depressible 2 (GCN2) and double stranded RNA dependent protein kinase (PKR)

In a primary embodiment, the methods of the invention are directed to inhibiting the PERK-phosphorylated-eIF2α-mediated integrated stress response. The inventors of the present disclosure have determined that this axis of the UPR is selectively triggered in tumor cells lacking PTEN and having activated Myc and that this results in activation of the PERK-mediated branch of the integrated stress response (ISR) While other branches of the UPR may be upregulated generally in response to tumors, the PERK-P-eIF2α ISR branch of the UPR is shown herein to be specifically and selectively activated in cells having PTEN loss and activated Myc.

Activated Myc results in elevated eIF2-P, the phosphorylated form of eukaryotic initiation factor (eIF2). This species is a key regulatory factor in the initiation of eukaryotic translation. In the unphosphorylated form, eIF2 (itself a heterodimer), forms a quaternary complex with other factors that may continue on to affect the translation of mRNAs. The formation of this complex is inhibited, however, when eIF2 is phosphorylated. eIF2 has a phosphorylation site on its alpha subunit, which may be acted on by any number of kinases which regulate translation. eIF2 may be phosphorylated by activated PERK (protein kinase RNA-like endoplasmic reticulum kinase), a regulatory element which itself is activated by ER stress.

In a first and general aspect, the scope of the invention encompasses a method of treating cancer by any process which inhibits the ability of PTEN- and Myc activated cells to adapt to the UPR stress induced by high levels of protein synthesis.

In a primary aspect, the scope of the invention encompasses the treatment of cancer in subjects having (or having had) cancerous cells, wherein the cancerous cells have both (1) PTEN loss and (2) activated Myc, by inhibition of the PERK-mediated ISR. Such inhibition may include any intervention that disrupts the activation, magnitude, or efficiency of adaptive response mediated by the PERK-eIF2 pathway.

The inhibition of the adaptive response may be achieved by various means, including by the administration of an agent comprising an inhibitor of the PERK-mediated ISR. As used herein, an "inhibitor of the PERK-mediated ISR" is an agent wherein the administration of the agent results in one or more effects such as: inhibition of phosphorylation of eIF2α by PERK;

depletion or inactivation of phosphorylated eIF2α;

an increase in the relative abundance of unphosphorylated eIF2α to phosphorylated eIF2α;

rendering cells insensitive to the effects of phosphorylated eIF2α;

promotion of the formation of the quaternary complex;

increase in the rate of protein synthesis in the cancerous cells; and increased levels of cancerous cell death caused by protein synthesis stress; and any other inhibition of the activation of the adaptive brake on global protein synthesis impacted by the PERK-mediated ISR.

In one embodiment, the inhibitor of the PERK-mediated ISR is an agent which renders cells insensitive to the effects of phosphorylated eIF2α. For example, In one embodiment, the agent which renders cells insensitive to the effects of eIF2α phosphorylation comprises ISRIB ("Integrated Stress Response inhibitor"), which is a potent and selective PERK inhibitor with IC50 of 5 nM. ISRIB increases the activity of the eIF2B guanosine recycling factor by stabilizing it into a decamer holoenzyme that enhances the binding of the eIF2 factor, thereby restoring protein synthesis regardless of eIF2α phosphorylation levels. The scope of the invention extends to the use of ISRIB variants and derivatives, for example, derivatives as described in U.S. Pat. No. 9,708,247, entitled "Modulators of the eIF2alpha pathway," by Walter et al.

In one embodiment, the PERK-eIF2 inhibitor comprises an inhibitor of PERK kinase activity. Exemplary inhibitors of PERK kinase activity include GSK2606414 and GSK2656157, and LY-4, as known in the art. In one embodiment, the PERK inhibitor is a composition described in U.S. Pat. No. 8,598,156, entitled "Chemical Compounds," by Axten et al. In one embodiment, the PERK-eIF2 inhibitor comprises a composition described in U.S. Pat. No. 9,668,662, entitled N-(2,3-dihydro-1H-pyrrolo[2,3-b]pyrdin-5-yl)-4-quinazolinamine and N-(2,3-dihydro-1H-indol-5-yl)-4-quinazolinamine derivatives as perk inhibitors, by Stansfield et al. In one embodiment, the inhibitor of PERK kinase activity comprises a composition described in Atkins et al., Characterization of a Novel PERK Kinase Inhibitor with Antitumor and Antiangiogenic Activity, 2013 Mar. 15; 73(6):1993-2002.

In some implementations of the invention, the inhibitor of PERK-mediated ISR comprises a composition which disrupts the adaptive response at the genetic level by targeting the expression of genes involved in the adaptive response. The inhibitor may comprise a species which disrupts a target gene, wherein the target gene comprises PERK, eIF2, ATF4 or any other element of the adaptive response. Exemplary compositions include TALENs, siRNA vectors, and CRISPR-Cas9 or like constructs directed to the selected target gene.

In some implementations, the inhibitor of PERK-mediated ISR comprises a composition which disrupts the adaptive response at the protein level by targeting the proteins involved in the adaptive response. The inhibitor may comprise a species which disrupts a target protein, wherein the target protein comprises PERK, eIF2, ATF4, or other elements of the adaptive response. Exemplary compositions include PROTEK or other selective ubiquitination complexes that selectively promote the degradation of PERK or eIF2-P. Agents may also comprise agents that bind to and inactivate or block access to active sites of target proteins. Exemplary species include aptamers, antibodies, and dominant negative mutants.

ATF4 Intervention.

The inventors of the present disclosure have further determined that activation of P-PERK and P-eIF2α results in the activation of ATF4, a known target of the PERK-P-eIF2α axis. ATF4 is selectively translated during eIF2α-induced global inhibition of protein synthesis and is a transcription factor that regulates a wide range of pro-adaptive genes which enable adaptation to stress conditions. The inventors of the present disclosure have demonstrated herein that ablation of ATF4 activity will result in tumor death. Accordingly, in one aspect, the scope of the invention encompasses treatments which inhibit (i.e. reduce the expression or activity) of ATF4. In one aspect, the scope of the invention comprises the administration of an agent comprising an inhibitor of the PERK-mediated ISR comprising an ATF4 inhibitor.

In one embodiment, the ATF4 inhibitor comprises ursolic acid or tomatidine, or a derivative thereof, or a compound disclosed in U.S. Pat. No. 9,034,299, entitled "ATF4 inhibitors and their use for neural protection, repair, regeneration, and plasticity," by Ratan; United States Patent Application Publication Number 20160317526, entitled, "Prolylhydroxylase/atf4 inhibitors and methods of use for treating neural cell injury or death and conditions resulting therefrom," by Ratan and Karuppagounder; and PCT International Patent Application Number WO2017212423, entitled "Chemical Compounds," by Axten et al.

Prognostic and Diagnostic Methods.

As above, the inventors of the present disclosure have determined that PTEN loss and Myc activation imparts a survival advantage by upregulation of the adaptive ISR. For example, as shown herein, in the case of prostate cancer, assessment of PTEN loss and activated Myc enables discrimination of individuals that will experience metastatic progression or prostate cancer-specific mortality. Accordingly, the present disclosures provide the art with a simplified, two-factor panel for prognosing various aspects of cancer pathology and progression.

Accordingly, the scope of the invention encompasses a method of determining a diagnostic status in a subject, comprising the steps of
   obtaining a sample from the subject, wherein the sample comprises cancerous cells;
   assessing PTEN loss and Myc activation in the cancerous cells; and
   if both PTEN loss and Myc activation are present, assigning an associated diagnostic status to the subject.
The diagnostic status may be any diagnostic or prognostic status associated with the combination of PTEN loss and Myc activation. For example, the diagnostic status may be any one or more of:
   amenability to treatment by inhibition of adaptive ISR;
   increased likelihood of cancer progression;
   increased likelihood of cancer recurrence;
   increased likelihood of cancer metastasis;
   increased likelihood of cancer mortality or decreased survival time.

The sample may comprise any relevant sample containing cancerous cells, including tumor biopsy, such as a punch biopsy, fine needle aspiration biopsy, needle core biopsy, bone biopsy or surgical specimen. The cancerous cells may comprise tumor cells, for example, primary tumor cells, cells from metastasis, etc. and precancerous cells, for example, putatively precancerous cells wherein tumorigenesis is not fully established.

The assessment of PTEN loss and Myc activation may be made by measurement of PTEN and Myc. Alternatively, phosphorylated eIF2α may be used as a measure of Myc activation, wherein elevated phosphorylated eIF2α is indicative of Myc activation.

Assessment of biomarker abundance may be performed by any appropriate method. In one implementation, expression levels or abundance are determined by direct measurement of expression at the protein or mRNA level, for example by microarray analysis, quantitative PCR analysis, or RNA sequencing analysis. Alternatively, labeled antibody systems may be used to quantify target protein abundance in the cells, followed by immunofluorescence analysis, such as FISH analysis.

In the case of PTEN, PTEN expression or PTEN protein levels may be assayed by appropriate methods known in the art. For example, PTEN may be quantified as described in United States Patent Application Publication Number 20100303809, entitled "Methods for the Detection and Quantitation of PTEN," by Bacus and Sakr et al., 2010, "Protocol for PTEN Expression by Immunohistochemistry in Formalin-fixed Paraffin-embedded Human Breast Carcinoma," Appl Immunohistochem Mol Morphol. 2010 July; 18(4): 371-374. PTEN expression can be assayed via immunohistochemistry (IHC) or immunofluorescence (IF) analysis and is quantifiable by mean fluorescence intensity, for example by comparing the differential expression of PTEN in stromal benign tissue to that of the cancerous cells.

In one implementation, eIF2α-P, the phosphorylated form of eIF2, is measured directly by immunohistochemistry or immunofluorescence (IF) for example, by using antibodies against phosphorylated forms of eIF2α protein. eIF2α-P may be assessed by any means known in the art, for example, as described in Teske et al., 2011, Methods in Enzymology, Chapter Nineteen—Methods for Analyzing eIF2 Kinases and Translational Control in the Unfolded Protein Response, Volume 490, pp 333-356 and Lobo et al., 2000, "Levels, Phosphorylation Status and Cellular Localization of Translational Factor EIF2 in Gastrointestinal Carcinomas," Histochemical Journal pp 139-150. Abundance may be quantified by mean fluorescence intensity, for example, by comparing the differential abundance of eIF2α in benign stroma and cancerous tissue.

In some embodiments, elevated eIF2-P may be assessed by measurement of Myc activation, for example by measurement of Myc gene expression or protein levels, wherein elevated Myc expression is indicative of activated elevated eIF2α-P. For example, Myc may be detected and quantified as described in Hilpert et al., 2001, "Anti-c-myc antibody 9E10: epitope key positions and variability characterized using peptide spot synthesis on cellulose," Protein Engineering, Design and Selection, Volume 14, Pages 803-806 and U.S. Pat. No. 4,918,162, "Assays and antibodies for N-MYC proteins," by Slalom. MYC protein level can be obtained by IF analysis and is quantifiable by mean fluorescence intensity by comparing the differential expression in benign stroma and cancerous tissue.

If the cells in the sample are determined to have both PTEN loss and elevated activated Myc, an associated diagnostic status may be assigned to the subject. Exemplary diagnostic status associated with PTEN loss and Myc activation include elevated risk for the development of cancer; elevated risk of cancer relapse; elevated risk of aggressive cancer; elevated risk of metastasis; elevated risk of cancer progression; or an increased likelihood that cancer that will respond to inhibitors of adaptive ISR. The risk factors may be assessed for subjects pre- or post-treatment, for example, In one embodiment, the factor is elevated risk of cancer recurrence progression in subjects having previously received curative treatment, such as surgery, radiation, chemotherapy, and/or immunotherapy.

The precise relationship between PTEN loss/activated Myc status and the selected diagnostic status may be established by any statistical method or model known in the art. For example, a classifier or other predictive model may be applied to the measured levels of PTEN and Myc or eIF2-P, for example, a classifier or predictive model generated using statistical methods such as: machine learning classifiers such as random forest, support vector machines, and newer deep learning and neural network approach and other statistical model generating methods known in the art. The output of the model may be a classification, score, or other output indicative of the subject's risk or probability of having the selected diagnostic status.

Upon determination that the cancerous cells of a subject have the PTEN loss/activated Myc phenotype, a suitable treatment may be administered. In one embodiment, the suitable treatment is the administration of an inhibitor of adaptive ISR. In one embodiment, the suitable treatment is a more aggressive treatment than would be administered to subjects with cancerous cells lacking the PTEN loss/activated Myc phenotype, for example, more aggressive surgical interventions, chemotherapeutic interventions, radiological interventions, or immunotherapy interventions, in line with the increased risk associated with the prosurvival phenotype.

Diagnostic Kits.

In one aspect, the scope of the invention comprises a diagnostic kit for the assessment of the PTEN loss and activated Myc phenotype. The diagnostic kit will comprise a collection of two or more compositions of matter directed to the detection and/or quantification of PTEN and Myc or eIF2-P in a sample. The two or more components may be packaged in a common packaging element, for example, a box, packet, or other common container. For example, the kit may comprise fluorescently labeled antibodies, or antibodies otherwise configured for immunofluorescent detection to PTEN and Myc or eIF2α-P, PCR primers for the amplification of PTEN and Myc or eIF2α in a sample, or other reagents for the selective amplification, labeling, or detection of PTEN and Myc or eIF2α-P. The kit may further comprise components for detection and/or quantification of PTEN and Myc or eIF2-P in a sample, for example, buffers, sample collection and analysis vessels, and software for analyzing images.

In one embodiment, the diagnostic kit comprises an antibody for the detection of PTEN and one of (1) an antibody for the detection of Myc or (2) an antibody for the detection of phosphorylated eIF2α.

EXAMPLES

Figure 1D:
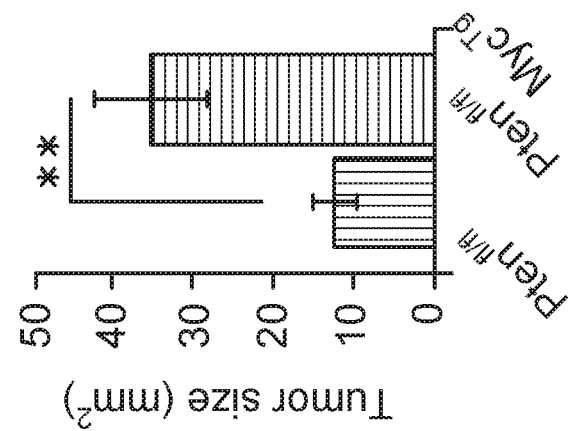
Figure 1C:
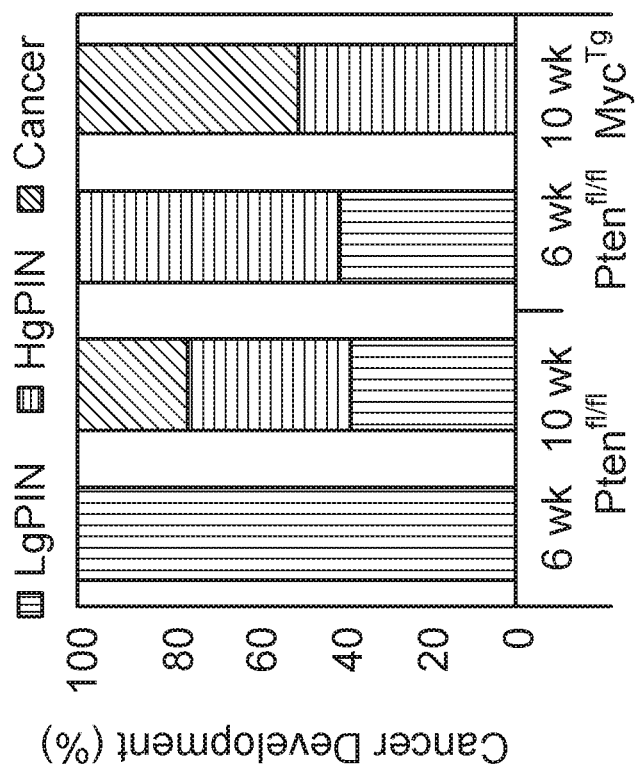
Figure 1E:
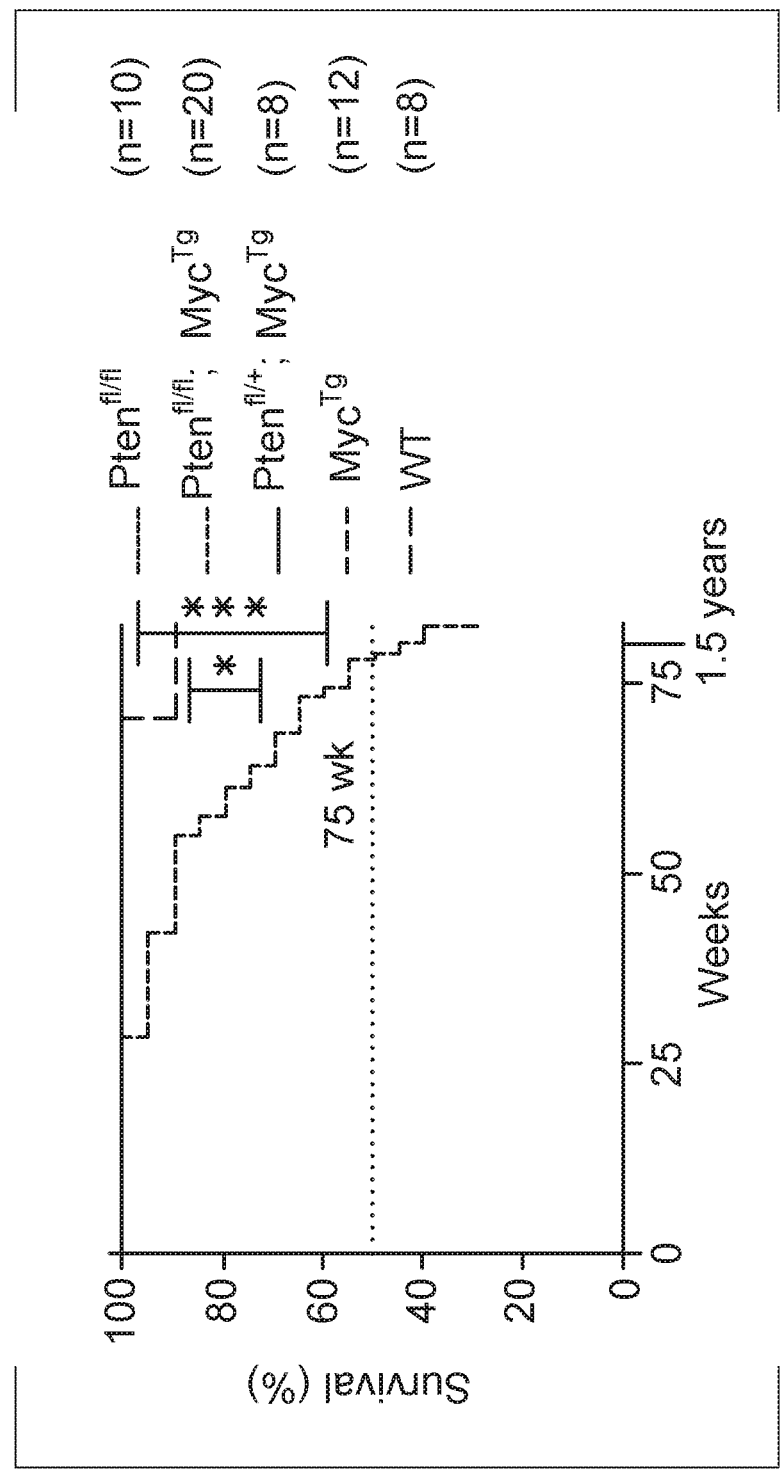

Example 1. MYC Amplification with PTEN Loss Diminish Oncogenic Increases of Global Protein Synthesis in Lethal Murine PCa Distinct stages of human PCa were modeled in the mouse, using a newly generated conditional transgenic MYC mouse, where the overexpression of C-MYC is driven in a Cre-specific manner ($Myc^{Tg}$), in combination with the conditional loss of PTEN in the prostate epithelium (Pb-cre4; $Pten^{fl/fl}$, herein referred to as $Pten^{fl/fl}$), as described in Lesche R, Groszer M, Gao J, Wang Y, Messing A, Sun H, Liu X, Wu H. Cre/loxP-mediated inactivation of the murine Pten tumor suppressor gene. Genesis. 2002; 32:148-149. [PubMed: 11857804]. The advantage of this mouse is that cells overexpressing $Myc^{Tg}$ can be traced through expression of green fluorescent protein (GFP) present in the targeting locus, allowing for visualization of the earliest events in tumorigenesis. In agreement with the notion that MYC hyperactivation may be a secondary event for human PCa development, it was observed that MYC overexpression alone in prostate epithelium (Pb-cre4; $Myc^{Tg}$, herein referred to as $Myc^{Tg}$) increased proliferation but did not result in adenocarcinoma by 1 year of age. This is consistent with previous reports, which showed MYC expression under the control of similar promoters to those used here. $Myc^{Tg}$ mice with concomitant loss of PTEN in prostate tissue ($Pten^{fl/fl}$; $Myc^{Tg}$) showed significant enlargement of prostate growth by 6 weeks of age (P<0.0003) and accelerated development of high-grade prostatic intraepithelial neoplasia (HgPIN) compared to mice with loss of PTEN alone. PTEN loss and MYC amplification cooperated to develop adenocarcinoma by 10 weeks (FIG. 1B), resulting in marked increases in $Pten^{fl/fl}$; $Myc^{Tg}$ tumor size visualized by ultrasound (FIG. 1C). This aggressive oncogenic progression significantly decreased overall survival (P<0.05), with a mean life span of 75 weeks (FIG. 1D). Collectively, this genetically engineered mouse model (GEMM) recapitulates aggressive human PCa and results in decreased survival.

To evaluate the effects of these key oncogenes on global protein synthesis, newly synthesized proteins were assessed by incorporation of $^{35}$S-labeled methionine in organoid cultures. Primary mouse three-dimensional organoid cultures were established to recapitulate the cellular environment of the murine prostate gland ex vivo. Organoids were derived from dissociated mouse prostate tissue containing a mixed population of luminal and basal cell types to mimic the histology observed in vivo. Western blot analysis confirmed that $Myc^{Tg}$ expression and PTEN loss were evident and associated with increased GFP expression and AKT phosphorylation. Consistent with the known ability of these major oncogenic pathways to increase protein synthesis, either loss of PTEN or MYC hyperactivation significantly increased global protein synthesis by about 20% (P<0.0003 for both). On the contrary, it was observed that an unanticipated but significant dampening in global protein synthesis occurred in Ptenfl/fl; MycTg mice (P=0.01), despite the fact that these mice developed more aggressive PCa (FIG. 1D). This observation revealed an interesting paradox. It suggested that despite the presence of two oncogenic lesions that individually up-regulate protein synthesis, an adaptive response appears activated when protein synthesis is up-regulated beyond a specific threshold in aggressive PCa.

Example 2. Aggressive PCa Activates a Key Cellular Stress Response During Tumor Development Proteins that are synthesized in the secretory pathway amount to about 30% of the total proteome in most eukaryotic cells. Although UPR activation can be studied with pharmacological inducers of ER stress, under physiological processes, the activation of the UPR may reduce the unfolded protein load through several prosurvival mechanisms, including the expansion of the ER membrane and the selective synthesis of key components of the protein folding and quality control machinery. To address how cancer cells respond and adapt to a protein synthesis burden in vivo and downstream of specific oncogenic lesions, it was tested whether a specific molecular signature of the UPR may be activated in $Pten^{fl/fl}$-versus $Pten^{fl/fl}$; $Myc^{Tg}$-derived PCa.

Figure 2:
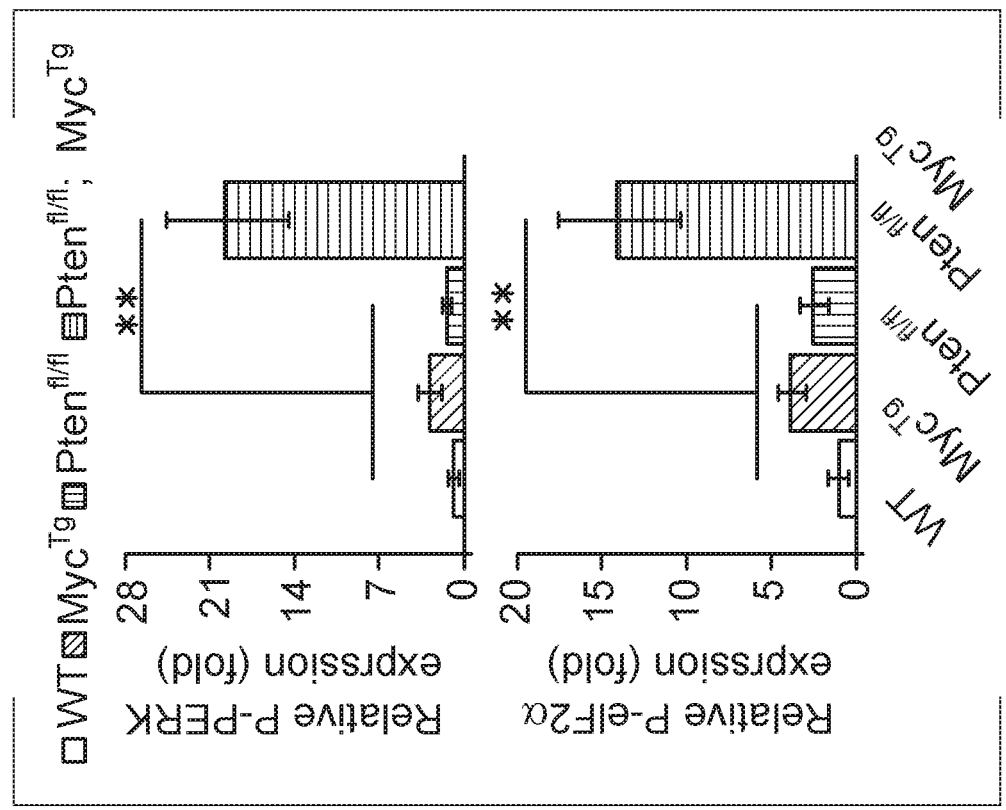
FIG. 2.
Figure 1F:
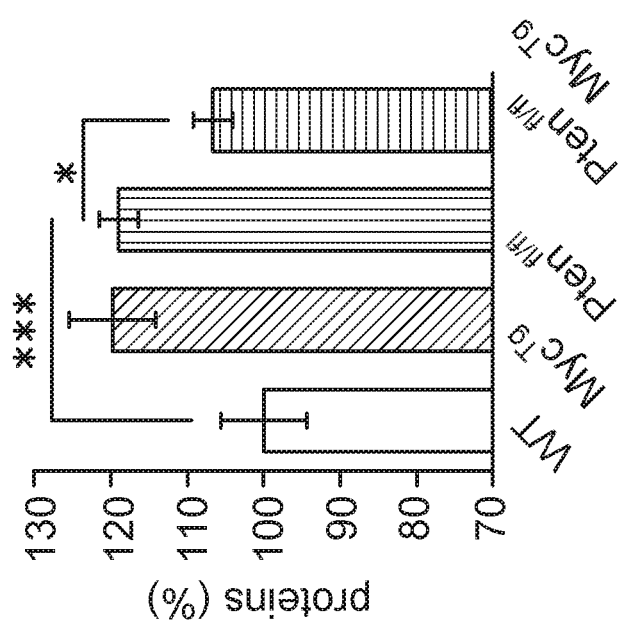

Quantitative immunofluorescence (IF) staining was performed for cleaved ATF6, P-IRE1, and P-PERK during tumor development to test whether the UPR was activated during PCa progression. Visualizing UPR expression within prostatic tissue at 10 weeks of age allowed direct assessment of the activity of each arm during neoplasia. Whereas the ATF6 and IRE1 branches of the UPR were relatively equally activated in $Pten^{fl/fl}$ and $Pten^{fl/fl}$; $Myc^{Tg}$ tissue, PERK phosphorylation was selectively increased by over 15-fold within $Pten^{fl/fl}$; $Myc^{Tg}$ tissue compared to its near absence in $Pten^{fl/fl}$ cells (FIG. 2). Thus, PERK activation is a distinct response that may promote tumorigenesis in aggressive PCa driven by the cooperation of two oncogenic lesions. To confirm the selective activation of PERK signaling in $Pten^{fl/fl}$; $Myc^{Tg}$ mice, the downstream signaling to eIF2α was evaluated. P-eIF2α was also markedly increased in $Pten^{fl/fl}$; $Myc^{Tg}$ mice and strongest within areas of PIN but remained absent within $Pten^{fl/fl}$ tissues (FIG. 2). The expression of the ER-specific molecular chaperone BiP was not changed and was also high in normal prostatic tissues in agreement with the secretory role of these glands. Collectively, this analysis reveals two independent, yet linked mechanisms: (i) activation of each UPR pathway in PCa in vivo and (ii) activation of a P-eIF2α-dependent response selectively in $Pten^{fl/fl}$; $Myc^{Tg}$ mice, which display more aggressive PCa progression and reduced survival.

Example 3. Rebalancing Protein Synthesis Through P-eIF2α is Required for Aggressive PCa Progression A general UPR response may promote adaptation to proteotoxic and ER stress, whereas the activation of P-eIF2α could place a direct brake on the overwhelming burden of protein synthesis that occurs during more aggressive tumorigenesis. To test this hypothesis, the organoid cultures were employed, which recapitulate the in vivo phenotype. The $Pten^{fl/fl}$; $Myc^{Tg}$ cultures showed increased activation of P-PERK, P-eIF2α, and expression of ATF4, which is a known target of the PERK-P-eIF2α axis (FIG. 3A). To determine whether the activation of this adaptive response was altering global protein synthesis, a small-molecule inhibitor of P-eIF2α activity, ISRIB was used, a compound that selectively reverses the effects of eIF2α phosphorylation. Specifically, P-eIF2α binds its dedicated guanine nucleotide exchanging factor (GEF), eIF2B, with enhanced affinity relative to eIF2α. Thus, P-eIF2α sequesters eIF2B from interacting with eIF2α to exchange guanosine diphosphate with guanosine triphosphate, which is an essential step to form the translation preinitiation complex. ISRIB increases eIF2B GEF activity by stabilizing it into a decamer holoenzyme to enhance the binding of the eIF2 factor, thereby restoring protein synthesis regardless of eIF2α phosphorylation. In $Pten^{fl/fl}$ organoid cultures, protein synthesis was not altered by ISRIB treatment, despite the drug inhibiting P-eIF2α activity, as confirmed by a decrease in ATF4 expression (FIG. 3A). Conversely, a marked increase of newly synthesized proteins was observed in $Pten^{fl/fl}$; $Myc^{Tg}$ cells, which show increased P-eIF2α signaling (FIG. 3A). Together, these experiments indicate that P-eIF2α creates an adaptive response to relieve the burden of increased protein synthesis within $Pten^{fl/fl}$; $Myc^{Tg}$ oncogenic cells.

In addition to PERK, other kinases can phosphorylate the eIF2α subunit upon distinct stress signals: GCN2 (amino acid deprivation), PKR (viral infection), and HRI (heme deprivation) (30). To assess whether the selective adaptive response observed during aggressive PCa development of $Pten^{fl/fl}$; $Myc^{Tg}$ mice was specific to the PERK-P-eIF2α axis, a genetic approach was employed, using $Perk^{fl/fl}$ mice to evaluate the loss of PERK in the prostate gland. $Pten^{fl/fl}$; $Myc^{Tg}$; $Perk^{fl/fl}$ mice showed markedly reduced prostate growth compared to $Pten^{fl/fl}$; $Myc^{Tg}$ mice, with weights similar to $Pten^{fl/fl}$ and $Pten^{fl/fl}$; $Perk^{fl/fl}$ mice at 10 weeks of age. The reduction in prostate size corresponded to a decrease in cancer progression and in cell proliferation. To determine the consequence of PERK loss for P-eIF2α signaling in PCa development, P-eIF2α expression was monitored by IF staining. The activation of P-eIF2α was reduced by 70% in $Pten^{fl/fl}$; $Myc^{Tg}$; $Perk^{fl/fl}$ tissue compared to $Pten^{fl/fl}$; $Myc^{Tg}$. These data strongly suggest that the P-eIF2α-dependent adaptive stress response is driven to a large extent by PERK signaling.

These studies demonstrated that P-eIF2α is directly activated in the early stage of $Pten^{fl/fl}$; $Myc^{Tg}$ tumorigenesis, being visible in benign tissue and increasing in HgPIN, which may reflect a distinct point of vulnerability for aggressive PCa. To evaluate the necessity of P-eIF2α for promoting tumor growth or maintenance in vivo, a preclinical trial was conducted. Mice with developed tumors were imaged by magnetic resonance imaging (MRI) to confirm a measurable baseline of prostate volume per mouse and then grouped into cohorts for either vehicle or ISRIB treatment daily over the course of 6 weeks. $Pten^{fl/fl}$; $Myc^{Tg}$ mice showed tumor regression within 3 weeks of ISRIB treatment, with no signs of toxicity, whereas all $Pten^{fl/fl}$ mice showed continued tumor growth (FIG. 3B).

By 6 weeks, $Pten^{fl/fl}$ mice showed an approximate 40% increase in growth over individual baseline measurements, whereas ISRIB-treated $Pten^{fl/fl}$; $Myc^{Tg}$ mice demonstrated no progression in tumor size. In addition, the immune cell infiltration was evaluated, marked by the pan-leukocyte antibody CD45 after 3 weeks of ISRIB treatment and observed no significant changes regardless of prostate tumor genotype and treatment. Further analysis of immune cell populations did not demonstrate substantial differences in total T cell or myeloid populations, including dendritic cells, macrophages, and neutrophils. Of the intertumoral immune cells examined, less than 5% were either $CD4^+$ or $CD8^+$ T cells, as expected for the $Pten^{fl/fl}$ murine prostate model. Although exclude the possibility that ISRIB may be remodeling tumor immunity during initial treatment may be considered, this was not evident after 3 weeks of treatment. Together, these studies reveal that P-eIF2α signaling is functionally relevant in aggressive PCa and that this adaptive response is therapeutically targetable in vivo using the small-molecule inhibitor ISRIB.

Figure 4A:
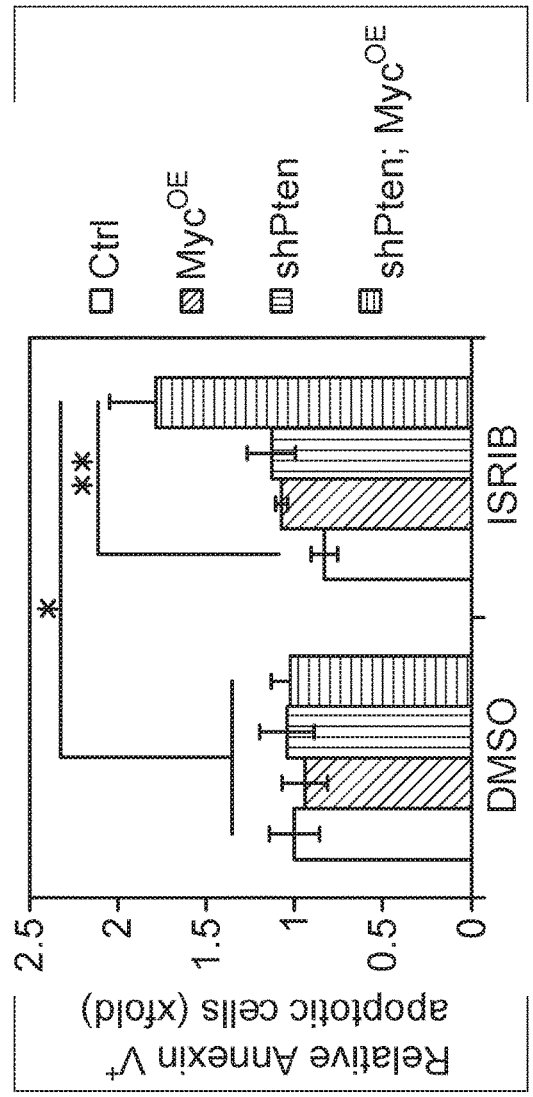
FIGS. 4A and 4B.

To extend these observations directly to human disease, human cell lines were created to mimic the genetic mouse models. Human RWPE-1 epithelial cells were created to stably knock down PTEN (shPTEN) with or without MYC overexpression. The combination of PTEN loss with increased MYC expression activated PERK signaling and P-eIF2α, showing that the adaptive response that we had observed in mice is also triggered in human prostate cells. To understand the requirement for this stress response checkpoint in human cells, each cell line was treated with ISRIB and observed a marked increase in apoptosis, independent of alterations in proliferation, specifically in shPTEN; $MYC^{OE}$ cells relative to control samples (FIG. 4A).

Example 4. High P-eIF2α Expression with Loss of PTEN is Associated with an Increased Risk of Metastasis after Surgery To further examine the clinical relevance of high P-eIF2α downstream of PTEN loss, a human tissue microarray (TMA) consisting of 424 tumors was made and analyzed the expression of PTEN, c-MYC, and P-eIF2α. On the basis of the GEMMs, it was predicted that the combination of PTEN loss and P-eIF2α would associate with advanced PCa. An array of patients was selected with PCa ranging from low to high risk, who received surgery as a curative treatment with a median of 10 years of follow-up to accurately evaluate the incidence of clinical progression, a composite outcome representing visceral or bone metastasis or PCa-specific mortality (MET/PCSM). Quantitative IF of P-eIF2α, c-MYC, and PTEN was normalized to adjacent benign tissue and then associated risk was evaluated for MET/PCSM. After controlling for age, prostate-specific antigen (PSA), Gleason score, and pathological staging, the analysis showed that patients with PTEN loss/high MYC expression were more likely to experience metastatic progression than patients with PTEN loss or high MYC alone.

Figure 4B:
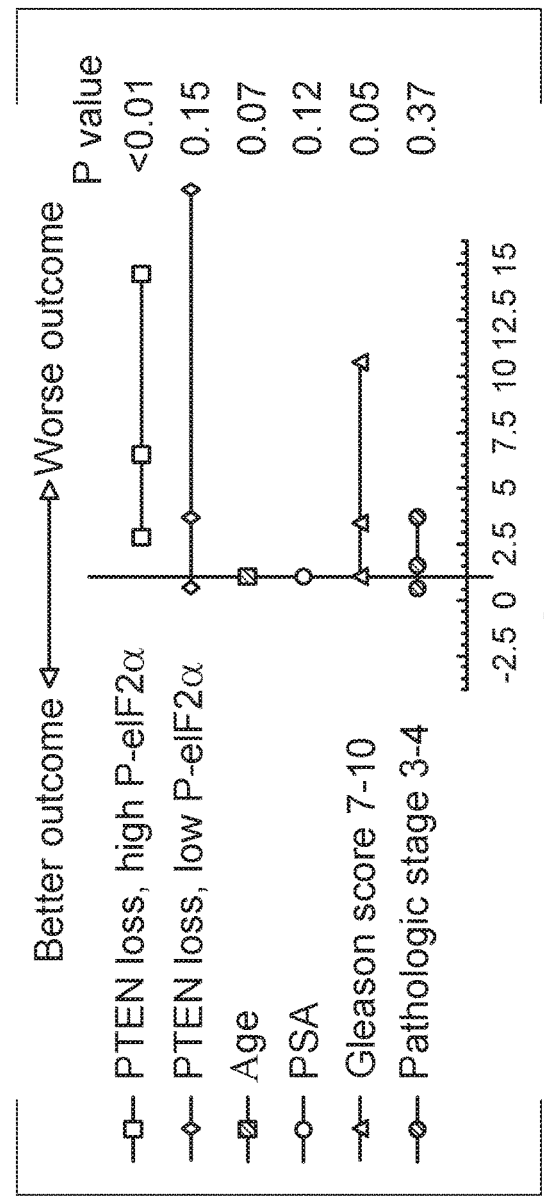

These data demonstrated that P-eIF2α is a targetable adaptive response downstream of PTEN loss and MYC hyperactivation. Hence, next examined was the associated risk of progression in patients with PTEN loss and high P-eIF2α at the time of surgery. The rate of MET/PCSM-free survival was significantly lower in patients with high P-eIF2α and PTEN loss compared to PTEN loss alone (P<0.01). Only 4% of patients with PTEN loss and low P-eIF2α succumbed to metastasis or death, whereas 19% of patients with PTEN loss and high P-eIF2α showed MET/PCSM by 10 years after surgical intervention with the intention to cure the disease. Furthermore, patients with high P-eIF2α and PTEN loss had a higher risk of MET/PCSM compared to patients with no PTEN loss, with a hazard ratio of 5.40 [95% confidence interval (CI), 2.46 to 11.86; P<0.01], whereas other variables that may affect the risk were not significantly different (FIG. 4B). MYC overexpression with either low or high P-eIF2α did not associate with increased risk of MET/PCSM, supporting the findings that MYC alone does not drive PCa. Notably, high P-eIF2α expression played a role equivalent to the MYC oncogene in combination with loss of PTEN at predicting metastatic progression, yet unlike MYC, P-eIF2α may be a druggable target. Together, the combination of P-eIF2α and PTEN loss thus serves as a predictor for cancer progression after curative treatment, which is independent of the traditional risk assessment system using PSA, cancer grade, and cancer stage.

Next was evaluated the discriminatory properties of high P-eIF2α and PTEN loss as a prognostic marker independent from the most commonly used risk assessment score in the clinic, CAPRA-S(Cancer of the Prostate Risk Assessment after Surgery). The c-index (concordance index) was used to evaluate the ability of the protein signature of high P-eIF2α with loss of PTEN to discriminate between individual patients who did or did not succumb to metastasis or death after surgery. Currently, clinicians depend on genomic risk to individualize treatment decisions using three available gene expression tests: PROLARIS™ (Myriad Genetics Inc.), DECIPHER™ (GenomeDX Inc), and ONCOTYPEDX™ (Genomic Health, Inc). The PROLARIS™ test relies on the average expression of 31 cell cycle progression (CCP) genes and was validated using the same cohort of patients used in the TMA. Within the same patients, the PROLARIS™-CCP panel has a combined c-index of 0.77 (CAPRA-S+CCP) (Cooperberg et al. Validation of a cell-cycle progression gene panel to improve risk stratification in a contemporary prostatectomy cohort. J Clin Oncol. 2013; 31:1428-1434. [PubMed: 23460710]), whereas high P-eIF2α and PTEN loss has a c-index of 0.80. These findings show that concurrent high P-eIF2α and PTEN loss serves as an independent predictor with improved prognostic accuracy over standard clinicopathologic testing for discriminating which individuals may experience metastatic progression.

Example 5. P-eIF2α is a Targetable Adaptive Response in Aggressive Human PCa Next, it was sought to functionally evaluate whether the UPR pathway could be targeted, specifically through P-eIF2α, in advanced human PCa. Although it is historically difficult to generate human prostate patient-derived xenograft (PDX) models, this was successfully achieved with similar characteristics to the Pten$^{fl/fl}$; Myc$^{Tg}$ mice to assess the effects of ISRIB on cancer growth and mortality. In particular, two PDX models were generated: one derived from a primary tumor, herein referred to as pPCa, and one derived from a lymph node metastasis in the left internal iliac chain from the same patient, herein referred to as mPCa. The pPCa-PDX tumor had significantly lower MYC expression than the mPCa-PDX tumor (P<0.01), but both showed loss of PTEN with increased P-AKT expression. A significant increase in P-eIF2α was observed only in the mPCa (P<0.01).

Figure 5A:
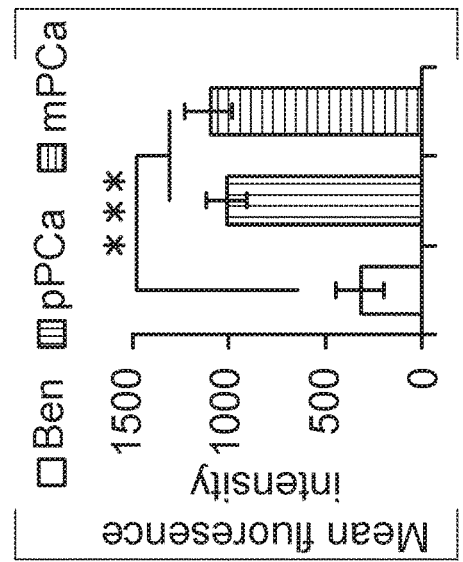
FIGS. 5A, 5B, 5C, 5D, 5E, 5F, and 5G.
Figure 5B:
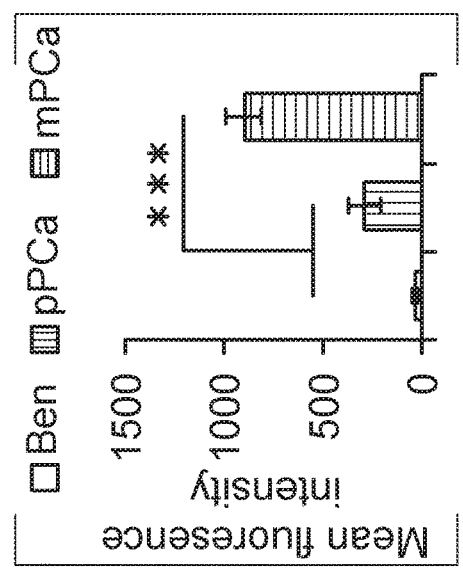
Figure 5C:
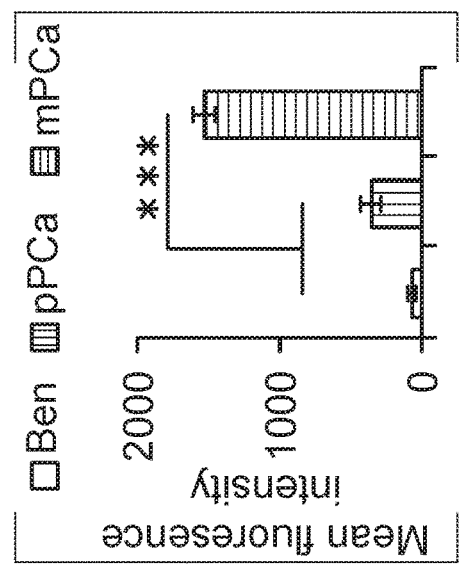
Figure 5E:
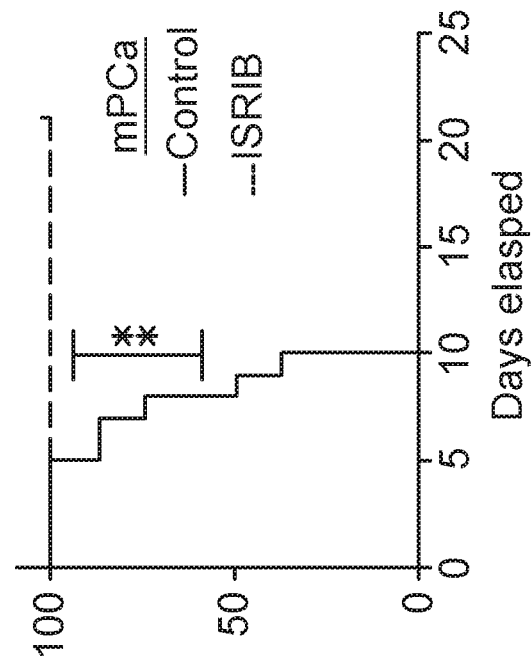
Figure 5D:
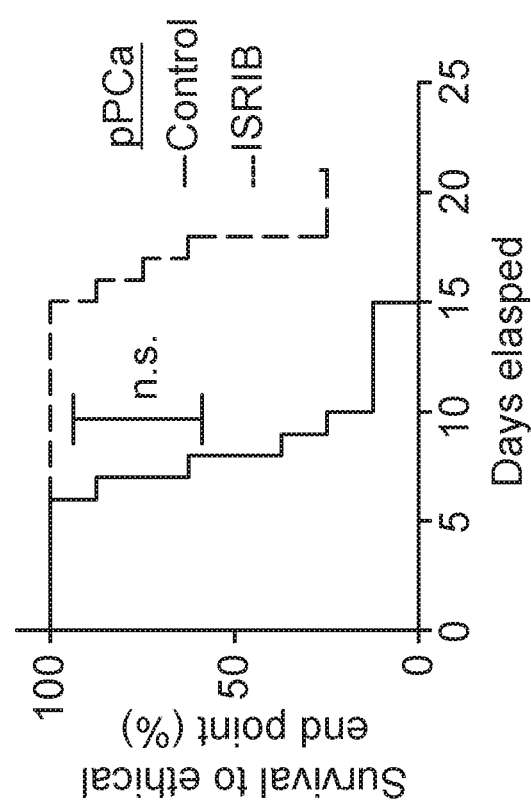

To test the therapeutic efficacy of ISRIB in human PCa, a preclinical trial was performed on the stably passaged PDX model. Targeting P-eIF2α pharmacologically significantly prolonged survival in mice bearing the metastatic tumor with high P-eIF2α (P<0.01; FIGS. 5D and 5E), whereas the effectiveness of ISRIB treatment was short-lived in pPCa tumor. Consistent with the GEM model, the mPCa-PDX model, with high expression of P-eIF2α, displayed significant tumor regression and cell death (P<0.01), as demonstrated by increased terminal deoxynucleotidyl transferase-mediated deoxyuridine triphosphate nick end labeling (TUNEL) staining and cleaved caspase 3 expression after only 9 days of ISRIB treatment (FIGS. 5, D and E, and FIG. S7B). Conversely, the pPCa-PDX model, with low P-eIF2α, did not show regression but stabilized with eventual tumor regrowth and no significant cell death. These findings demonstrate that attenuating P-eIF2α activity with ISRIB elicits a potent antitumor effect in a humanized model of advanced PCa.

Figure 5G:
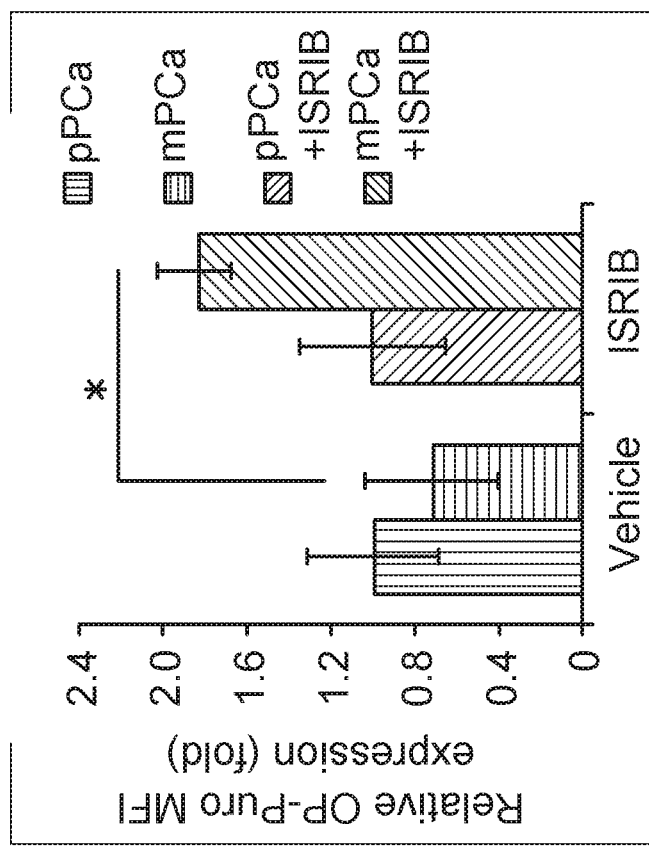
Figure 5F:
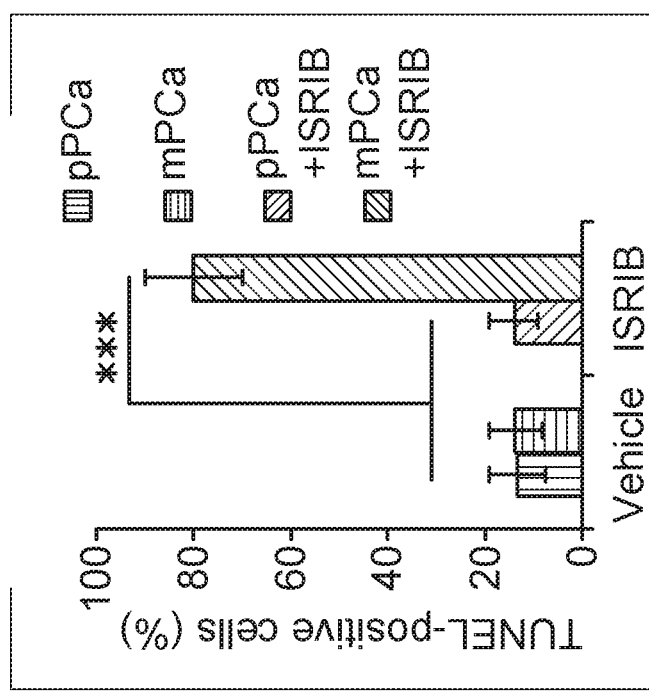

Next, it was determined whether a metastatic PCa tumor, harboring high MYC and loss of PTEN activity in a complex genetic background of human PCa, relies on eIF2α phosphorylation as an adaptive response to restrain global protein synthesis. Therefore, newly synthesized proteins in vivo were assessed by measuring the incorporation of O-propargyl-puromycin (OP-Puro) within the primary and metastatic tumor-derived PDXs, which have low or high P-eIF2α, respectively. Upon ISRIB treatment, a marked increase was observed in global protein synthesis specifically in the mPCa PDX, but no change in pPCa tumors where P-eIF2α expression was not up-regulated (FIG. 5G). To further assess the functional relevance of P-eIF2α signaling, ATF4 expression was decreased in vivo using intratumor knockdown by small interfering RNA (siRNA). Within the area of intratumor ATF4 loss, apoptosis and decreased proliferation assessed by TUNEL and Ki67 staining of mPCa PDX was observed. This demonstrated that inhibition of the PERK-eIF2α axis by a genetic or pharmacological approach effectively results in cell death of aggressive PCa in vivo.

Example 6. Targeting P-eIF2α Activity Reduced Metastasis and Prolonged Survival in a PDX Model of Metastatic Castration-Resistant PCa In hormone-sensitive metastatic PCa, androgen deprivation therapy (ADT) remains the mainstay treatment; however, these tumors inevitably develop resistance to ADT and progress into the lethal form of metastatic castration-resistant PCa (mCRPC). Characterization of the hormone-sensitive metastatic disease has not been predictive of outcomes in the clinical setting of lethal mCRPC. To directly study the contribution of P-eIF2α to metastasis, an additional PDX (herein mCRPC PDX) was generated derived from a patient with mCRPC despite prolonged treatment with complete androgen blockage using leuprolide (ADT) and antiandrogen therapy (enzalutamide). Three weeks after implantation of the mCRPC tumor under the mouse renal capsule, tumor dissemination to the liver, distant kidney, lymph nodes, and spleen was observed. The mCRPC PDX line continued to exhibit metastatic dissemination in the mouse host after multiple passages and retained histological and molecular characteristics of the original tumor. The distant metastatic lesions exhibited loss of PTEN, high MYC, and high P-eIF2α expression.

To examine the role of P-eIF2α from the early stages of metastatic growth to late stages of dissemination, a prostate-specific membrane antigen [$^{68}$Ga-PSMA-11 PET/computed tomography (CT)] scan was used to trace the progression of very small metastases from early to late stages of dissemination, which were not visible by conventional imaging modalities such as $^{18}$F-DG PET/CT. Prostate-specific membrane antigen (PSMA) is highly expressed on the surface of PCa cells and allows sensitive staging to evaluate therapy response in the clinical setting. Mice bearing liver or distal metastasis (confirmed by PSMA PET) were treated with either vehicle or ISRIB. Inhibition of P-eIF2α with ISRIB significantly prolonged survival in mCRPC PDX mice bearing distal metastatic lesions (P=0.01). In contrast, mice with metastasis died within 10 days on vehicle treatment. By direct imaging with PSMA PET/CT, substantial metastatic regression was observed at distal sites in mice treated with ISRIB. In addition, a difference in metastatic progression in the liver was confirmed by pathohistological analysis at time of euthanasia. Therefore, two independent PDX models of metastatic disease, one derived from a patient with early nodal metastasis (hormone-sensitive) and the second from a patient with castration-resistant PCa, demonstrated that blocking the activation of the adaptive brake on global protein synthesis via the P-eIF2α axis resulted in profound tumor regression and inhibition of metastatic dissemination.

Example 7. Discussion

The data disclosed herein reveal a cell-autonomous mechanism wherein the activity of two major oncogenic lesions, loss of PTEN and MYC overexpression, which independently enhance protein synthesis, paradoxically, decrease global protein production when these oncogenic events coexist. This highlights the requirement for an adaptive protein homeostasis response to sustain aggressive tumor development.

Proteostasis is essential for normal cell health and viability, and as such is ensured by the coordinated control of protein synthesis, folding, and degradation. Although the UPR enables proteostasis to be restored during unfavorable conditions, herein is demonstrated that PCa cells have usurped a specific branch of this pathway for tumor growth and maintenance. The UPR consists of three main branches, yet only the PERK-P-eIF2α axis is selectively triggered in this pathophysiological state to ensure continued survival of cancer cells. The adaptive response involving P-eIF2α signaling provides a barrier to uncontrolled increases in protein synthesis and creates a permissive environment for continued tumor growth.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of treating cancer in a subject, comprising the steps of:
   obtaining a sample comprising cancerous cells from the subject;
   assessing PTEN loss in the cancerous cells;
   assessing Myc activation in the cancerous cells; and
   wherein, if both PTEN loss and Myc activation in the cancerous cells is observed, administering to the subject a pharmaceutically active amount of an agent which inhibits the PERK-mediated integrated stress response, wherein the cancerous cells of the subject comprise prostate cancer cells.

2. The method of claim 1, wherein
   the agent which inhibits the PERK-mediated integrated stress response comprises an agent which renders cells insensitive to the effects of eIF2α phosphorylation.

3. The method of claim 2, wherein
   the agent which inhibits the PERK-mediated integrated stress response comprises ISRIB.

4. The method of claim 1, wherein
   the agent which inhibits the PERK-mediated integrated stress response comprises an inhibitor of PERK expression, translation, or kinase activity.

5. The method of claim 4, wherein
   the inhibitor of PERK expression, translation, or kinase activity comprises GSK2606414 or GSK2656157.

6. The method of claim 1, wherein
   the agent which inhibits the PERK-mediated integrated stress response is an ATF4 inhibitor.

* * * * *

UNITED STATES PATENT AND TRADEMARK OFFICE
CERTIFICATE OF CORRECTION

| | |
|---|---|
| PATENT NO. | : 11,253,522 B2 |
| APPLICATION NO. | : 16/396723 |
| DATED | : February 22, 2022 |
| INVENTOR(S) | : Davide Ruggero et al. |

It is certified that error appears in the above-identified patent and that said Letters Patent is hereby corrected as shown below:

In the Specification

At Column 1, Line 17:
"This invention was made with government support under grant number R01 CA154916 awarded by the National Institutes of Health. The government has certain rights in the invention."

Should be:
"This invention was made with government support under W81XWH-15-1-0460 awarded by the Medical Research and Development Command, and R01 CA154916 awarded by the National Institutes of Health. The government has certain rights in the invention."

Signed and Sealed this
Fourth Day of June, 2024

Katherine Kelly Vidal
*Director of the United States Patent and Trademark Office*